United States Patent [19]
Berry et al.

[11] Patent Number: 5,098,376
[45] Date of Patent: Mar. 24, 1992

[54] APPARATUS AND METHODS FOR FURLING AND INTRODUCING AN EXTRAPULMONARY BLOOD GAS EXCHANGE DEVICE

[75] Inventors: Gaylord L. Berry, Salt Lake City; J. D. Mortensen, Sandy; Mitchell D. Baldwin, Salt Lake City, all of Utah

[73] Assignee: Cardiopulmonics, Inc., Salt Lake City, Utah

[21] Appl. No.: 454,773

[22] Filed: Dec. 22, 1989

[51] Int. Cl.$^5$ .............................................. A61M 37/00
[52] U.S. Cl. ...................................... 604/26; 604/109; 604/43; 604/49; 604/165
[58] Field of Search .................................. 604/24–26, 604/95, 96, 264, 280, 283, 104–109, 43–45, 49, 53, 158, 164, 165, 171; 606/191, 198

[56] References Cited

U.S. PATENT DOCUMENTS

| | | | |
|---|---|---|---|
| 2,389,355 | 4/1945 | Goland et al. | 604/165 |
| 3,505,686 | 4/1970 | Bodell | 623/66 |
| 3,552,384 | 1/1971 | Pierie | 604/95 X |
| 3,794,468 | 2/1974 | Leonard et al. | 23/258.5 |
| 3,856,475 | 12/1974 | Marx . | |
| 4,231,878 | 11/1980 | Esmond | 422/48 |
| 4,239,729 | 12/1980 | Hasegawa et al. | 422/48 |
| 4,252,122 | 2/1981 | Halvorsen | 604/264 X |
| 4,265,249 | 5/1981 | Schindler et al. | 128/635 |
| 4,268,279 | 5/1981 | Shindo et al. | 55/16 |
| 4,306,018 | 12/1981 | Kirkpatrick | 435/2 |
| 4,374,802 | 2/1983 | Fukasawa | 422/48 |
| 4,376,095 | 3/1983 | Hasegawa | 422/46 |
| 4,387,711 | 6/1983 | Merry | 128/207.15 |
| 4,576,590 | 3/1986 | Fiddian-Green | 604/26 |
| 4,583,969 | 4/1986 | Mortensen | 604/49 |
| 4,631,053 | 12/1986 | Taheri | 604/49 |
| 4,655,748 | 4/1987 | Mushika | 604/96 |
| 4,664,113 | 5/1987 | Frisbie et al. | 604/96 X |
| 4,682,981 | 7/1987 | Suzuki et al. | 604/158 |
| 4,717,379 | 1/1988 | Ekholmer | 604/43 |
| 4,726,374 | 2/1988 | Bales et al. | 604/108 |
| 4,824,435 | 4/1989 | Giesy et al. | 604/49 |
| 4,846,174 | 7/1989 | Willard et al. | 604/95 X |
| 4,850,958 | 7/1989 | Berry et al. | 604/26 |
| 4,874,371 | 10/1989 | Comben et al. | 604/95 |
| 4,911,689 | 3/1990 | Hattler | 604/26 |
| 4,928,693 | 5/1990 | Goodin et al. | 128/637 |
| 4,950,224 | 8/1990 | Gorsuch et al. | 604/4 |

FOREIGN PATENT DOCUMENTS

1280481  11/1961  France ............................... 604/101

OTHER PUBLICATIONS

Bodell et al., "A Capillary Membrane Oxygenator," J. Thoracic and Cardiovas. Surg. 46:639 (1963).
Bodell, "An Implantable Artificial Lung," JAMA 191:125 (Jan. 25, 1965).
Galletti et al., "Development of an Implantable Booster Lung," Trans. ASAIO 24:573 (1980).
Tanishita et al., "Augmentation of Gas Transfer with Pulsatile Flow in the Coiled Tube Membrane Oxygenator Design," Trans ASAIO 26:526 (1980).

(List continued on next page.)

Primary Examiner—John D. Yasko
Assistant Examiner—Adam J. Cermak
Attorney, Agent, or Firm—Workman, Nydegger & Jensen

[57] ABSTRACT

An in vivo extrapulmonary blood gas exchange device is disclosed having a hollow fiber bundle in gaseous communication with a coaxial dual lumen tube and having a furling apparatus for twisting one coaxial lumen relative to the other. The furling apparatus enables the outside diameter of the bundle of gas permeable tubes to be selectively adjusted to provide either a furled, small insertion diameter when inserting the apparatus into the venae cavae of a patient or an unfurled, expanded oxygenation diameter after the apparatus is in place within the venae cavae and the bundle of gas permeable tubes is deployed therein. The oxygenator is inserted into the patient through a single incision at one of the right external iliac, common femoral, or internal jugular veins. A novel distal tip configuration permits the oxygenator to be inserted into the patient utilizing an over-the-guidewire intravascular insertion technique.

43 Claims, 4 Drawing Sheets

OTHER PUBLICATIONS

Barthelemy et al., "Total Extracorporeal $CO_2$ Removal in a Pumpless Artery-to-Wein Shunt," Trans ASAIO 28:354 (1982).

Kolobow et al., "Carbon Dioxide and the Membrane Artificial Lung: Their Roles in the Prevention and Treatment of Respiratory Failure," Trans ASAIO 28:20 (1982).

Phillips et al., "Percutaneous Initiation of Cardiopulmonary Bypass," Annals of Thoracic Surg. 36:223 (1983).

Mortensen, J. D., "An Intravenacaval Blood Gas Exchange (IVCBGE) Device," vol. XXXIII Trans. Am. Soc. Artif. Intern. Organs (1987).

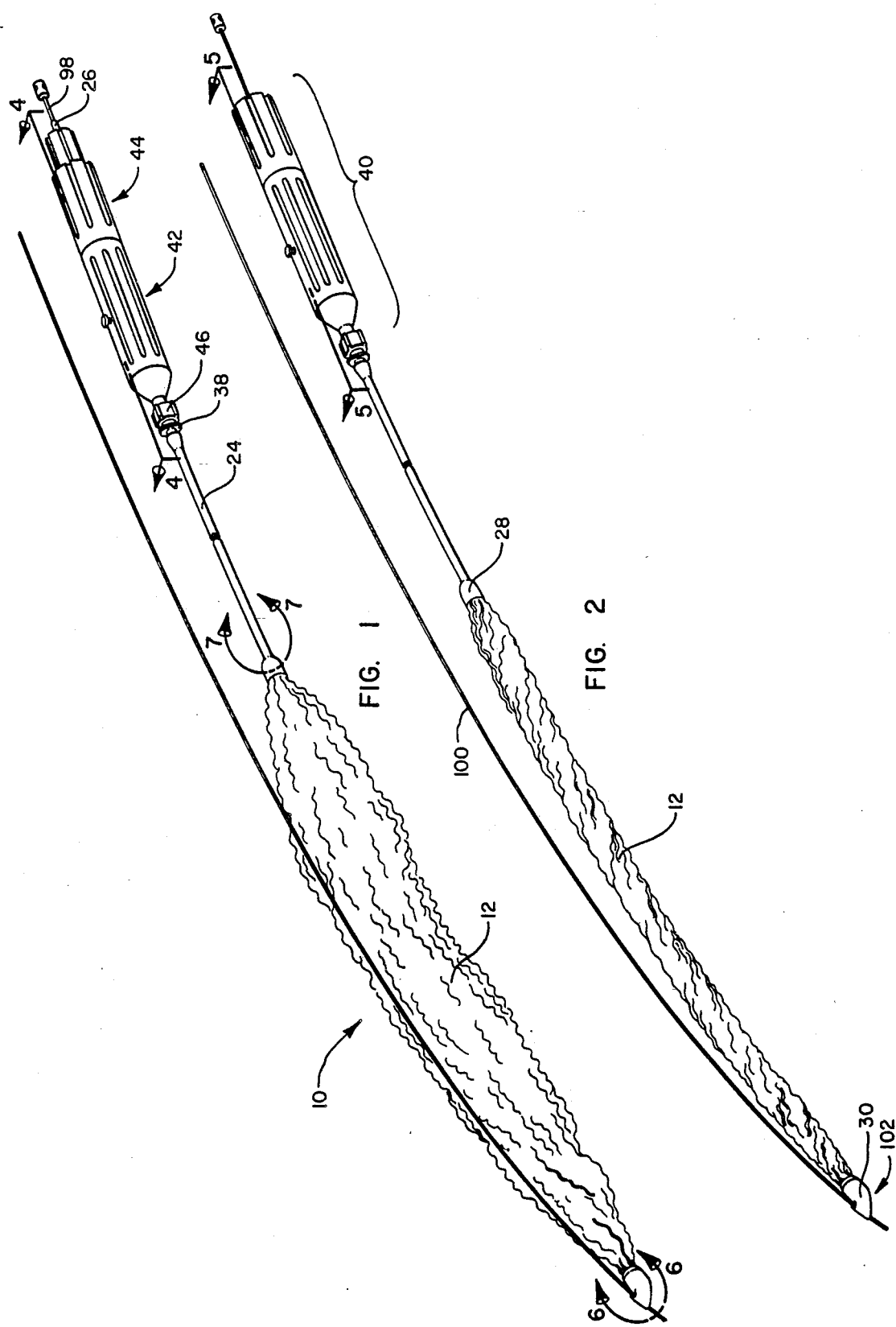

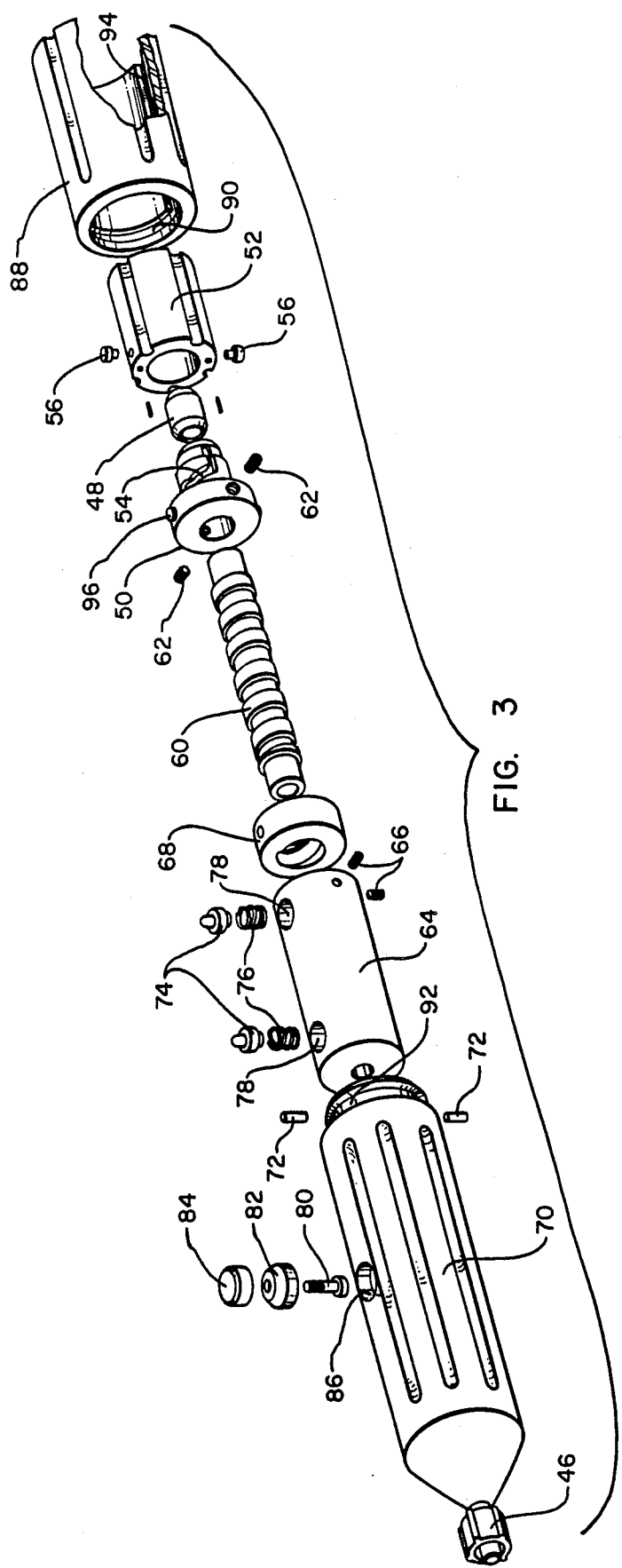
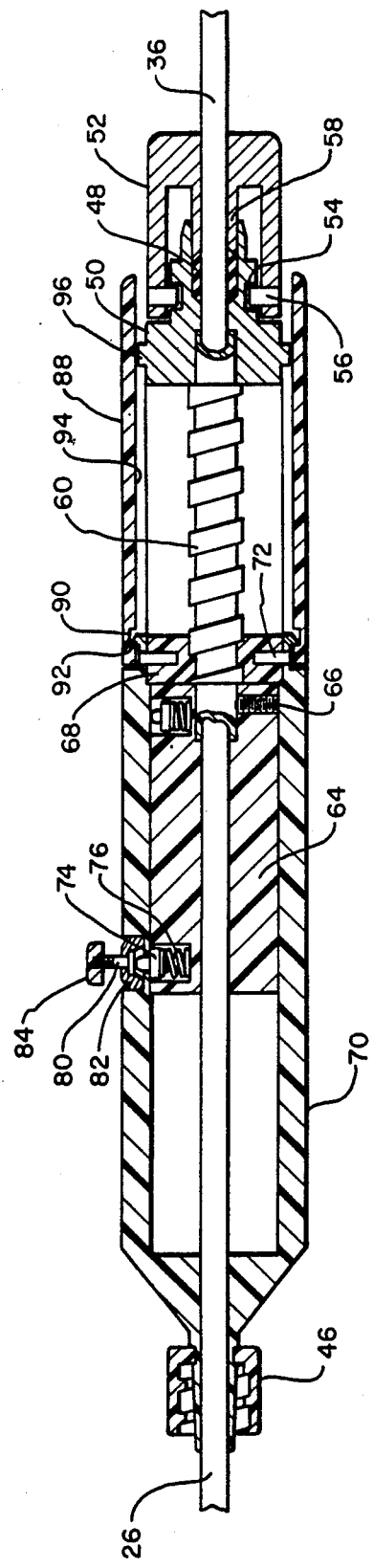

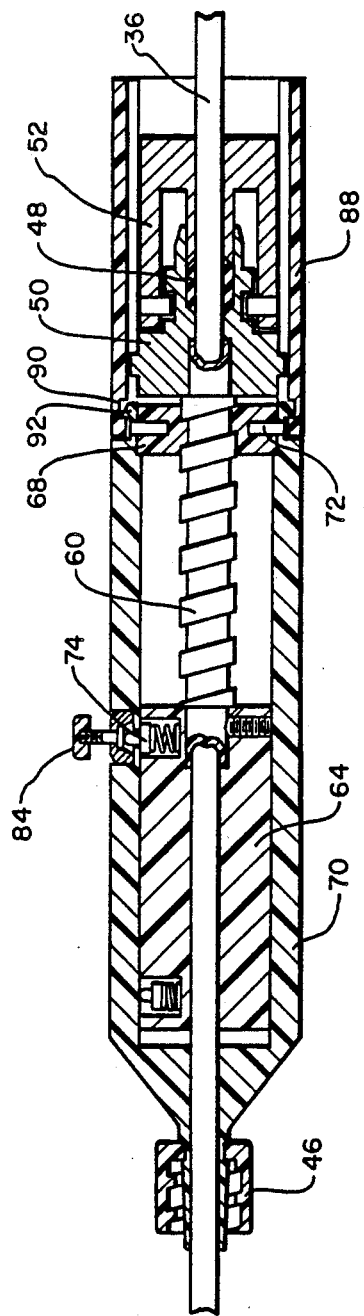
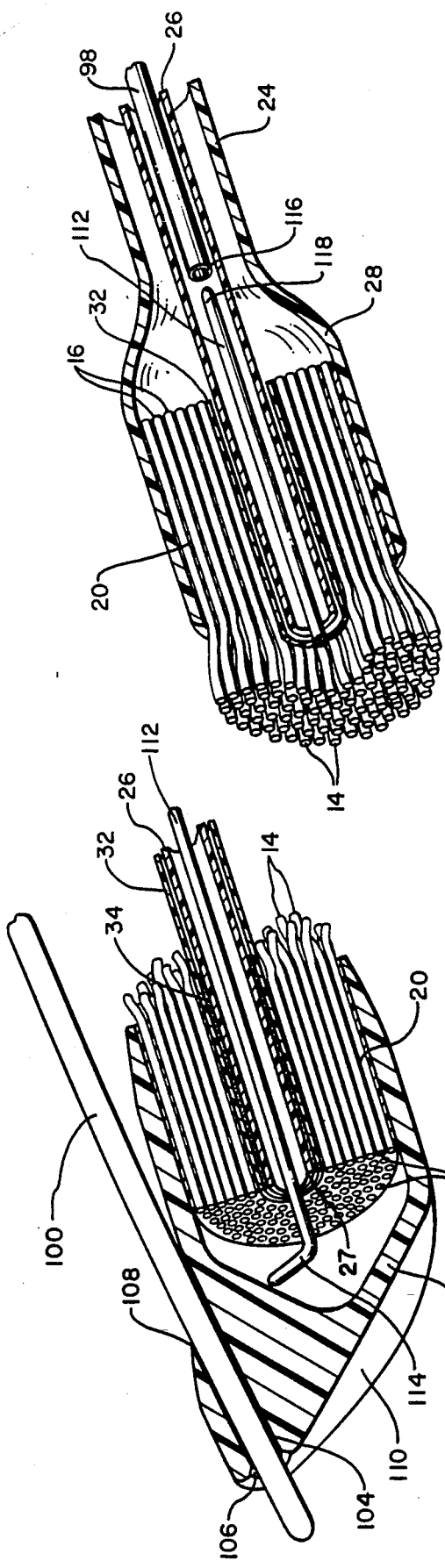
FIG. 5
FIG. 7
FIG. 6

APPARATUS AND METHODS FOR FURLING AND INTRODUCING AN EXTRAPULMONARY BLOOD GAS EXCHANGE DEVICE

BACKGROUND

1. Field of the Invention

The present invention relates to apparatus and methods for twisting one coaxial lumen relative to the other. The present invention also relates to a medical apparatus tip for over-the-guidewire intravenous insertion of the apparatus. More particularly, the present invention is directed to apparatus and methods for furling and introducing an extrapulmonary blood gas exchange device in order to perform extrapulmonary blood gas exchange.

2. Technology Review

Thousands of patients in hospitals suffer from inadequate blood gas exchange, which includes both inadequate blood oxygenation and inadequate removal of carbon dioxide ($CO_2$). These conditions are commonly caused by varying degrees of respiratory inadequacy usually associated with acute lung illnesses such as pneumonitis, atelectasis, fluid in the lung, or obstruction of pulmonary ventilation. Various heart and circulatory aliments such as heart disease and shock can adversely affect the flow of blood and thereby also reduce the rate of blood gas exchange.

Currently the most widely used methods of treating these types of blood gas exchange inadequacies involve increasing the flow of oxygen through the lungs by either increasing the oxygen concentration of the inspired gases or by mechanically ventilating the lungs. Both methods result in placing further strain on the lungs, which may be diseased and unable to function at full capacity. In order to allow diseased or injured organs to heal it is generally best to allow these organs a period of rest followed by a gradual increase in activity. The current methods of treating inadequate blood gas exchange, however, force the diseased or damaged lungs to work even harder rather than allowing them a period of rest and recovery.

Various devices have been developed which are capable, at least for a limited period of time, of taking over the gas exchange function of the lungs. Many extracorporeal blood oxygenators are in common use and are employed most frequently during heart surgery. These devices are capable of providing blood oxygenation sufficient to carry the patient through the surgical procedure. These oxygenators include devices which bubble oxygen into the blood as the blood flows through the device. This is usually followed by a section of the device which defoams the blood to make it acceptable for reinjection into the patient.

Another group of extracorporeal oxygenators employ gas permeable membranes. These devices take many different shapes and configurations; however, the basic concept of operation is the same in all of these devices. Blood flows on one side of the gas permeable membranes while an oxygen rich gas flows on the other side of the membrane. As the blood flows through the device, the oxygen travels across the gas permeable membrane and enters the blood. This allows oxygenation of the blood without actually introducing oxygen bubbles into the blood and without the corresponding need for an extensive defoaming apparatus.

Gas permeable membranes used in such extracorporeal oxygenators are of two types. One type uses a microporous membrane which allows blood gas interface through micropores in the membrane. The other type is a continuous membrane which does not have micropores but which allows blood gas exchange through the membrane without the blood gas interface.

The microporous and bubble oxygenators discussed above are not suited for use outside the setting of a cardiopulmonary bypass procedure, and are thus typically designed for short term extracorporeal use. As a result, these devices are of limited use in the long term intensive care of respiratory failure patients.

In vivo extrapulmonary blood gas exchange has been demonstrated in the art. One known device, described in U.S. Pat. No. 4,850,958 which is incorporated herein by specific reference, consists of a plurality of elongated gas permeable tubes being bound at each end and enclosed within a respective air tight proximal and distal chamber. A dual lumen tube having an outer lumen and an inner lumen is situated relative to the gas permeable tubes such that the outer lumen terminates within the proximal chamber and such that the inner lumen terminates within the distal chamber.

The overall, outside diameter of the bundle of gas permeable tubes is selectively adjusted to provide either a furled, small insertion diameter when inserting the apparatus into the venae cavae of a patient or an unfurled, expanded oxygenation diameter after the apparatus is in place within the venae cavae and the bundle of gas permeable tubes is deployed therein. One of either the inner and outer lumens are connected to a source of oxygen rich gas. The other lumen is connected to an exhaust tube or other means for allowing the gas to flow out of the device.

U.S. Pat. No. 4,850,958 describes a device and method for furling the bundle of gas permeable tubes. The distal chamber is twisted relative to the proximal chamber by means of a stylet which passes through the inner lumen and engages the distal end of the inner lumen. Because the inner lumen is nonrotatably secured to the distal chamber, twisting the stylet simultaneously twists the distal chamber. Thus, by twisting the stylet relative to the proximal chamber, the distal chamber is twisted, thereby twisting the bundle of gas permeable tubes.

While the method of inserting this extrapulmonary blood gas exchange device within a patient's venae cavae has been successfully demonstrated, still there are some drawbacks. First, the need for a stylet which engages the distal end of the inner lumen in order to place the apparatus in a furled, insertion diameter means that the stylet must be fully inserted within the inner lumen during insertion. When the stylet extends fully to the distal end of the inner lumen, the flexibility of the distal end is substantially reduced. In practice, a rigid distal end is more difficult to insert through the patient's winding vascular system and is more likely to cause trauma to the sensitive intimal tissues of the patient's venous system.

Second, the furling device described in U.S. Pat. No. 4,850,958 did not provide any mechanism for indicating when the apparatus was fully furled and for preventing excessive furling. It has been found that the gas permeable tubes may be damaged by over-twisting.

Another significant drawback with the described furling device is the risk of sudden and undesired unwinding, for example, during insertion. If the stylet were accidentally released while the bundle of gas permeable tubes was fully twisted, the bundle would naturally unwind. This is a serious problem if the apparatus is in the process of being inserted into the patient's venae cavae. The risk exists because the screw for securing the stylet is always exposed to potential release during the insertion procedure.

A serious drawback also exists with the current apparatus insertion method. Due to the large size of the apparatus, a guidance system is needed to guide the apparatus through the peripheral venous system into the venae cavae. A common prior art system for introducing catheters and the like within a patient's vascular system is the "over-the-guidewire" technique (sometimes referred to as "OTG"). In this technique, a thin guidewire (typically a "J-tip" spring guidewire) is inserted into the vessel and guided to the desired location. The catheter or other device is then inserted over the guide wire, thereby following the guidewire to the desired location. Once the device is in place, the guidewire is withdrawn.

The OTG insertion technique may only be used with a device that has on open distal end. For this reason, the OTG method has been used primarily for open ended catheters and similar devices. It will be appreciated that the intravenous oxygenation device described in U.S. Pat. No. 4,850,958 does not have an open distal end and therefore could not be used with the OTG insertion method.

BRIEF SUMMARY AND OBJECTS OF THE INVENTION

The present invention seeks to resolve a number of the problems which have been experienced in the art, as identified above. More specifically, the apparatus and method of this invention constitute an important advance in the art of extrapulmonary blood gas exchange, as evidenced by the following objects and advantages realized by the invention over the prior art.

One object of the present invention is an apparatus and method for furling an intravenous blood gas exchange device in which a stylet is not required to engage and twist the distal end of the device in order to form an insertion diameter or an oxygenation diameter.

Additionally, it is an object of the present invention to provide an apparatus for furling an intravenous blood gas exchange device which indicates when the device is fully furled and fully unfurled, thereby reducing the risk of potential damage to the gas permeable tubes caused by over-twisting.

Still an additional object of the present invention is to provide an apparatus for furling an intravenous blood gas exchange device which prevents sudden and undesired unfurling of the bundle of gas permeable tubes.

Another object of the present invention is to provide apparatus and methods for inserting an intravenous blood gas exchange device in which the flexibility of the distal end may be adjusted during insertion.

Still a further important object of the present invention is an apparatus for in vivo blood oxygenation capable of being inserted with an over-the-guidewire insertion method.

Additional objects and advantages of the invention will be apparent from the description which follows, or may be learned by the practice of the invention.

Briefly summarized, the foregoing objects and advantages are realized by the apparatus and methods of the present invention. One embodiment within the scope of the present invention is broadly directed to an apparatus for twisting one lumen of a coaxial lumen device relative to the other lumen. Another embodiment of the present invention is directed to a medical apparatus tip for over-the-guidewire insertion of the apparatus into a patient. These embodiments are particularly adapted for use with an intravenous blood oxygenation device, such as those described in U.S. Pat. No. 4,850,958.

A typical intravenous blood oxygenation device of the present invention includes a dual lumen tube containing two coaxial lumens. The outer lumen opens into a proximal chamber to which a plurality of gas permeable tubes are attached. The inner lumen of the dual lumen tube extends past the outer lumen and passes among the gas permeable tubes. Both the inner lumen and the gas permeable tubes open into a distal chamber.

The gas permeable tubes are crimped to form the tubes into a wavy pattern in order to maintain the tubes in a spaced relation one from another so that the blood may flow freely between and around the tubes thereby enhancing blood surface contact with the gas permeable tubes. In addition, the wavy pattern of the gas permeable tubes tend to inhibit laminar blood flow between and around the tubes so as to cause disturbed flow of blood over the tubes.

The apparatus is inserted into a patient through an incision made in either the common femoral vein, external iliac vein or internal jugular vein. Before insertion, the distal chamber is preferably twisted relative to the proximal chamber. In this way, the gas permeable tubes are stretched and held tightly together so that the overall diameter of the device is smaller than its untwisted diameter.

The distal chamber preferably defines a short conduit formed therein which extends from a distal point on the distal chamber to a proximal point on the distal chamber. The conduit is oriented in a manner such that the conduit may be passed over a guidewire while the guidewire remains substantially exterior of the oxygenation apparatus. In this way, the apparatus may be inserted into the patient using a guidewire to direct the apparatus to the desired location. After insertion into the venae cavae, the guidewire is removed and the distal chamber is allowed to unwind so that the gas permeable tubes fill the venae cavae.

The distal chamber is twisted relative to the proximal chamber by means of a novel furling apparatus within the scope of the present invention. The furling apparatus includes a device for removably engaging the proximal end of the inner lumen, a device for removably engaging the proximal end of the outer lumen, and a device for twisting the inner lumen relative to the outer lumen. Because the inner lumen is nonrotatably secured to the distal chamber, twisting the inner lumen simultaneously twists the distal chamber. Likewise, the outer lumen is nonrotatably secured to the proximal chamber. Thus, by twisting the inner lumen relative to the outer lumen, the distal chamber is twisted relative to the proximal chamber, and the gas permeable tubes are placed in either a twisted state, thereby forming an insertion diameter, or an untwisted state, thereby forming an oxygenation diameter.

The furling apparatus within the scope of the present invention preferably includes a mechanism for indicating when the extrapulmonary oxygenation device is fully furled and fully unfurled. One embodiment providing this feature has a locking pin which automatically locks the furling apparatus when the device is furled and unfurled. Thus, in order to furl an unfurled device, the locking pin must be disengaged; likewise, in order to unfurl a furled device, the locking pin must be disengaged.

The furling apparatus also prevents sudden and undesired unfurling of the bundle of gas permeable tubes. This important advantage is achieved by preventing the furling apparatus from disengaging the inner lumen when the extrapulmonary oxygenation device is fully furled. One method for providing this feature is to retract the portion of apparatus which engages the proximal end of the inner lumen within the portion of the apparatus which twists the inner lumen, as the inner lumen is twisted. By the time the oxygenation device is fully furled, the device which releasably engages the inner lumen is not accessible for disengagement.

An important feature of the present invention is the ability to removably insert a stylet within the inner lumen even when the gas permeable tubes are twisted into an insertion diameter. It has been found that the closer the distal end of the stylet gets to the distal chamber, the stiffer the distal end of the in vivo extrapulmonary oxygenation apparatus becomes. Thus, the rigidity of the apparatus may be adjusted, even during insertion, by sliding the stylet in or out of the inner lumen.

After the extrapulmonary oxygenation apparatus is inserted within the patient, one of either the first or second lumens is connected to a source of oxygen rich gas. The other lumen is connected to an exhaust tube or other means for allowing the gas to flow out of the device. The oxygen rich gas flows into the gas permeable tubes. As venous blood flows around the gas permeable tubes, oxygen passes from the tubes into the blood causing blood oxygenation, and carbon dioxide passes from the blood into the tubes and out of the body. Gas flow through the tubes is augmented and risk of air embolism is eliminated by applying suction to the exhaust tube. The tubes are constructed of a material which allows efficient gas transfer yet is impervious to blood and is also relatively nonthrombogenic.

BRIEF DESCRIPTION OF THE DRAWINGS

In order to more fully understand the manner in which the above-recited advantages and objects of the invention are obtained, a more particular description of the invention will be rendered by reference to specific embodiments thereof which are illustrated in the appended drawings. Understanding that these drawings depict only one or more typical embodiments of the invention and are therefore not to be considered limiting of its scope, the presently preferred embodiments and the presently understood best mode of the invention will be described with additional detail through use of the accompanying drawings in which:

FIG. 1 is a perspective view of one presently preferred embodiment within the scope of the present invention in which the gas permeable tubes are untwisted to form an expanded oxygenation diameter with respect to the outside diameter of the overall bundle of tubes;

FIG. 2 is a perspective view of the embodiment of the present invention illustrated in FIG. 1 in which the gas permeable tubes are twisted and elongated to form a small insertion diameter with respect to the outside diameter of the overall bundle of tubes;

FIG. 3 is an exploded perspective view of the furling apparatus within the scope of the present invention;

FIG. 4 is an enlarged cross-sectional view of the furling apparatus shown in FIG. 1 taken along line 4—4;

FIG. 5 is an enlarged cross-sectional view of the furling apparatus shown in FIG. 2 taken along line 5—5;

FIG. 6 is an enlarged perspective cross-sectional view of the over-the-guidewire distal tip configuration of the embodiment illustrated in FIG. 1 taken along line 6—6;

FIG. 7 is an enlarged perspective cross-sectional view of a portion of embodiment illustrated in FIG. 1 taken along line 7—7;

DETAILED DESCRIPTION OF THE PREFERRED EMBODIMENTS

A. The Extrapulmonary Blood Oxygenator

Figure 8:
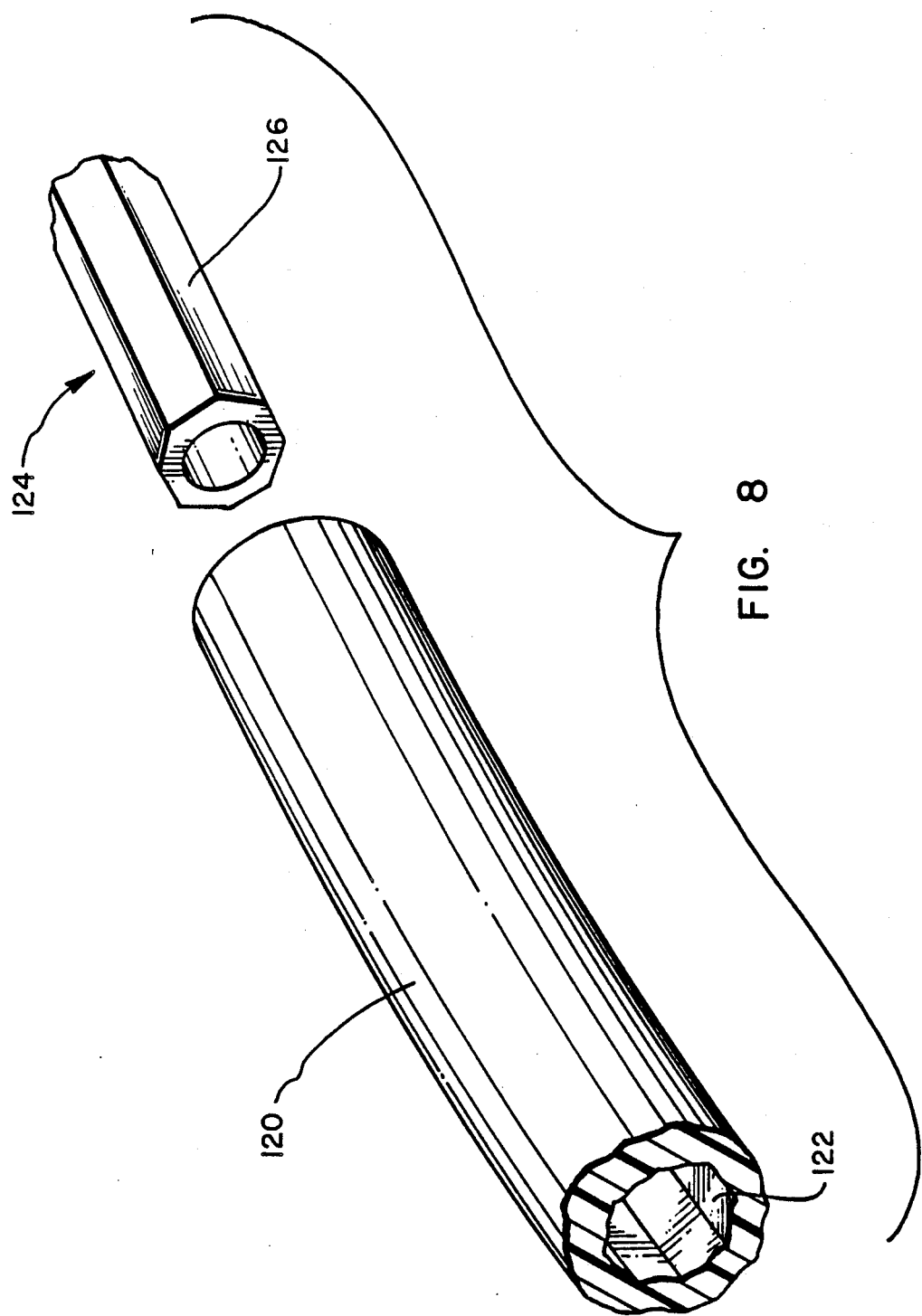
FIG. 8 is an enlarged perspective view of one possible mechanism for engaging the proximal end of the inner lumen within the scope of the present invention.

Reference is now made to the drawings wherein like parts are designated with like numerals throughout.

Referring first to FIGS. 1 and 2, extrapulmonary blood oxygenator 10 includes a hollow fiber bundle 12 comprised of a plurality of elongated gas permeable tubes, sometimes referred to as hollow fibers. Individual gas permeable tubes 14, shown best in FIGS. 6 and 7, each have a proximal end 16 and a distal end 18. Both the proximal ends and the distal ends of the gas permeable tubes are bound tightly together with a potting agent 20.

The extrapulmonary blood oxygenator 10, which is more fully described in U.S. Pat. No. 4,850,958, includes a coaxial dual lumen tube having an inner lumen 26 and an outer lumen 24. The inner lumen 26 extends the length of the gas permeable tubes 14, such that the inner lumen terminates adjacent the distal ends 18 of tubes 14, while the outer lumen 24 terminates adjacent the proximal ends 16 of tubes 14.

The in vivo extrapulmonary blood oxygenator of the present invention permits oxygen to be introduced into the gas permeable tubes and carbon dioxide to be collected as it exits the gas permeable tubes. This function is preferably accomplished by enclosing the proximal and distal ends of the gas permeable tubes so as to form airtight chambers. By also enclosing the distal ends of the outer and inner lumen within the airtight chambers, the gas permeable tubes are in gaseous communication with the outer and inner lumens.

As illustrated in FIG. 7, one means for enclosing the proximal ends 16 of the gas permeable tubes 14 comprises a proximal chamber 28. As shown, proximal chamber 28 is preferably formed from the distal end of outer lumen 24. The proximal chamber 28 is airtight such that the outer lumen 24 is in gaseous communication with the bound proximal ends 16 of the gas permeable tubes.

Similarly, as shown in FIG. 6, one means for enclosing the distal ends 18 of gas permeable tubes 14 comprises distal chamber 30 which also encloses the distal end 27 of inner lumen 26. The distal chamber 30 is airtight such that the bound distal ends 18 of the gas permeable tubes 14 are in gaseous communication with the inner lumen 26.

In the embodiment illustrated in FIGS. 6 and 7, a flexible spacer lumen 32 is bound together with the proximal and distal cylindrical ends 16 and 18. Spacer lumen 32 extends between the proximal and distal chambers 28 and 30, and the spacer lumen terminates at approximately the same point the proximal ends 16 and distal ends 18 of the gas permeable tubes terminate.

The ends of the gas permeable tubes and the flexible spacer lumen 32 are preferably bound with potting agent 20 that produces an airtight bond between the gas permeable tubes and the spacer lumen 32. Airtightness is a critical safety consideration because the extrapulmonary blood oxygenator should not introduce air bubbles within the blood stream. If air bubbles are introduced into the patient's blood stream, there is a serious risk of air embolism formation which can be fatal.

As illustrated in FIG. 6, the inner lumen 26 is bound to flexible spacer lumen 32 with bonding agent 34. In this way, the inner lumen is nonrotatably bound to distal ends 18 of the gas permeable tubes. Bonding agent 34 is preferably a material capable of bonding the inner lumen 26 to the spacer lumen 32. The bonding agent should be able to maintain an airtight seal despite a warm and humid in vivo environment. In addition, the bonding agent 34 should be able to withstand sterilization. One presently preferred bonding agent is an epoxy resin.

Because the flexible spacer lumen 32 is bound to both the proximal and distal ends of the gas permeable tubes, the spacer lumen is twisted as the gas permeable tubes are twisted. Therefore, the spacer lumen should preferably be constructed of a material which may be twisted. In addition, the flexible spacer lumen should be constructed of a material which can be securely bound with the gas permeable tubes.

One presently preferred material for constructing the flexible spacer lumen 32 is polyurethane due to its high elasticity and compatibility with the preferred polyurethane potting compound. Other possible suitable materials for constructing the spacer lumen are polyvinyl chloride and silicone. However, the choice of spacer lumen determines to a large extent what potting compound will be suitable. For example, if spacer lumen 32 is constructed of silicone, it would be necessary to use a silicone potting compound in order to form an adequate airtight bond between the ends of the gas permeable tubes and the spacer lumen.

Because gas transfer is a primary function of the extrapulmonary blood oxygenator, the gas transfer surface area in contact with the blood is preferably maximized. To increase the gas transfer surface area without unduly increasing the size of the apparatus, a large number of very small diameter gas permeable tubes (also referred to as hollow fibers) are used. In addition, the gas permeable tubes are preferably thin-walled in order to enhance gas permeability.

The total number of tubes and the cross-sectional diameter of each tube are both considered in determining a preferred operating embodiment of the in vivo apparatus. The apparatus must be small enough to be inserted into the venae cavae through a smaller peripheral vein, yet have a large enough gas transfer surface to achieve the desired blood gas exchange. Thus, as the cross-sectional diameter of the gas permeable tubes increases, the total number of tubes which can be used decreases.

Each gas permeable tube 14 preferably has an outside diameter in the range from about 200 microns to about 350 microns. Depending upon the size of the patient (i.e., whether infant or adult) and the amount of oxygenation therefore required, the number of gas permeable tubes 14 will vary. For example, in applications for the apparatuses to be used with infants, typically the apparatus would contain approximately 90 tubes. For applications of the apparatus which are intended for use with adults, up to 1500 tubes may be used.

The gas permeable tubes are preferably maintained in a spaced relation one from another such that the blood surface contact with the gas permeable tubes is maximized and such that laminar blood flow between and around the tubes is inhibited and disturbed blood flow over the tubes is achieved. To achieve this in one preferred embodiment of the present invention, the gas permeable tubes include a plurality of crimps which form the tubes 14 into a wavy pattern. The crimps of the gas permeable tubes 14 also aid in permitting the tubes to be slightly stretched as they are twisted so as to elongate the hollow fiber bundle 12 when it is desired to narrow the overall outside diameter of the hollow fiber bundle 12 for purposes of forming the insertion diameter as described herein.

Since the gas permeable tubes will be in contact with flowing blood, it is critical to minimize thrombosis formation. As a result, the gas permeable tubes are preferably constructed of a thrombo-resistant material. In one embodiment of the present invention, the gas permeable tubes include a support material of microporous hollow polypropylene fibers coated with a thin siloxane polymer. The siloxane is relatively nonthrombogenic. However, in a preferred embodiment the siloxane surface is coated with thrombo-resistant materials to further minimize thrombosis formation.

B. The Furling Apparatus

The extrapulmonary blood oxygenator illustrated in FIGS. 1 and 2 is designed for in vivo extrapulmonary blood gas exchange within the venae cavae of a patient. To use the apparatus in vivo, the overall outside diameter with respect to the hollow fiber bundle 12 should be sufficiently small to be inserted within the venae cavae through a peripheral vein, yet sufficiently large to fill the venae cavae cross-section once the hollow fiber bundle 12 is deployed therein. To achieve both of these objectives, the overall diameter of the hollow fiber bundle may be selectively adjusted to provide either a small insertion diameter (illustrated in FIG. 2) when inserting the apparatus within the venae cavae or an expanded oxygenation diameter (illustrated in FIG. 1) after the apparatus is in place within the venae cavae.

To selectively adjust the overall outside diameter of the hollow fiber bundle 12, the gas permeable tubes comprising the bundle are twisted and elongated. The overall outside diameter of the hollow fiber bundle is adjusted by twisting either the bound proximal ends 16 or the bound distal ends 18 of the gas permeable tubes relative to each other.

The means for selectively adjusting the overall diameter of the gas permeable tubes within the scope of the present invention preferably includes means for releasably engaging the proximal end 36 of the inner lumen 26, means for releasably engaging the proximal end 38 of outer lumen 24, and means for twisting one lumen relative to the other lumen. Because the inner lumen 26 is nonrotatably secured to the distal chamber 30, twisting the inner lumen simultaneously twists the distal chamber. Likewise, the outer lumen 24 is nonrotatably secured to the proximal chamber 28. Thus, by twisting the inner lumen relative to the outer lumen, for example, the distal chamber is twisted relative to the proximal chamber, and the gas permeable tubes forming the hollow fiber bundle are twisted and elongated, thereby forming an insertion diameter, or untwisted and deployed, thereby forming an oxygenation diameter.

One preferred means for selectively adjusting the overall diameter of the gas permeable tubes is illustrated in FIGS. 1-5. Furling apparatus 40 within the scope of the present invention is shown attached to the extrapulmonary blood oxygenator 10 in FIGS. 1 and 2 and is shown in exploded perspective and cross-sectional views in FIGS. 3-5.

As shown in FIGS. 1 and 2, furling apparatus 40 includes stationary member 42 and twisting member 44. A lock nut 46 secured to stationary member 42 releasably engages the proximal end 38 of outer lumen 24. Because the proximal chamber 28 is integral with outer lumen 24, the proximal chamber may be held relatively stationary by engaging the proximal end 38 using lock nut 46 and holding stationary member 42 relatively stationary.

Twisting member 44 includes means for releasably engaging the proximal end of the inner lumen. One currently preferred method of releasably engaging the inner lumen is by compressing a compressible gasket positioned around the inner lumen. As shown in FIGS. 3-5, the furling apparatus 40 includes a hollow elastomeric gasket 48 which is configured to be positioned around the inner lumen. Means for compressing gasket 48 are also provided by the furling apparatus.

One possible compression means within the scope of the present invention includes a collet 50 and a locking hub 52. Both collet 50 and locking hub are generally cylindrical in shape and have a hollow center through which the inner lumen may pass. Collet 50 defines a pair of matching spiral grooves 54 on the outer surface thereof. Locking hub 52 has two spiral tracking pins 56 which are configured to fit within the spiral grooves 54. As shown best in FIGS. 4 and 5, the elastomeric gasket 48 fits within the hollow portion of collet 50. The spiral groove portion of the collet is positioned within the locking hub 52 such that spiral tracking pins 56 fit within spiral grooves 54. The locking hub also includes a center piston 58 which fits within the hollow portion of collet 50.

Both collet 50 and center piston 58 are preferably tapered at the point of contact with elastomeric gasket 48 such that movement of collet 50 and center piston 58 towards each other compresses the elastomeric gasket 48 towards inner lumen 26. This may be conveniently accomplished by twisting locking hub 52 relative to collet 50 such that the spiral tracking pins 56 follow the spiral groove 54. The spiral groove 54 is preferably configured so that the elastomeric gasket is maintained in a compressed state when locking hub 52 is fully twisted relative to collet 50.

As shown in FIGS. 3-5, collet 50 is secured to the proximal end of leadscrew 60 with set screw 62. The distal end of leadscrew 60 is secured to traveler cylinder 64 with two set screws 66. Leadscrew 60 is threadably engaged with leadscrew nut 68 positioned between collet 50 and traveler cylinder 64. Leadscrew nut 68 is secured to the proximal end of traveler housing 70 with two locking pins 72. Hence, the combination of locking hub 52, elastomeric gasket 48, collet 50, leadscrew 60 and traveler cylinder 64 is threadably connected to the combination of leadscrew nut 68, traveler housing 70, and lock nut 46. Therefore, it will be appreciated that the proximal end of inner lumen 26 may be releasably engaged by the elastomeric gasket/collet/locking hub combination and that the proximal end of the outer lumen 24 may be releasably engaged by the lock nut/traveler housing combination, which combinations are threadably connected by the leadscrew and leadscrew nut.

It will be appreciated that there are other possible means for releasably engaging the proximal end of the inner lumen. In another embodiment within the scope of the present invention, the means for releasably engaging the proximal end of the inner lumen includes an inner lumen having a noncircular inner surface cross-sectional configuration and a mandrel having a matching outer surface cross-sectional configuration. The mandrel is inserted within the inner lumen and engages the inner lumen such that by twisting the mandrel, the inner lumen is twisted. FIG. 8 illustrates one possible configuration of this embodiment.

As shown in FIG. 8, the proximal end of inner lumen 120 has a noncircular inner surface 122 cross-sectional configuration. Mandrel 124 has a matching outer surface 126 cross-sectional configuration such that the mandrel is capable of removable insertion within the proximal end of inner lumen 120. Because the inner surface of the inner lumen and the outer surface of the mandrel have matching noncircular cross-sectional configurations, the mandrel engages the inner lumen upon insertion therein. Accordingly, the inner lumen is twisted by twisting the mandrel.

As discussed in greater detail below, it is important to allow a stylet to be inserted and removed while the in vivo extrapulmonary blood oxygenator is fully twisted. Therefore, mandrel 124 is preferably hollow to permit insertion and removal of a stylet while the mandrel engages the proximal end of the inner lumen.

The mandrel is preferably part of a twisting member (not shown) within the scope of the present invention which functions in cooperation with a stationary member (not shown) to selectively adjust the overall diameter of an in vivo extrapulmonary blood oxygenator. It will be appreciated that based upon the foregoing teachings, one may modify the furling apparatus described above to use a mandrel which engages the inner surface of the inner lumen for the purpose of releasably engaging the proximal end of the inner lumen.

The furling apparatus within the scope of the present invention preferably includes a mechanism for indicating when the extrapulmonary oxygenation device is fully furled and fully unfurled. One embodiment providing this feature has a locking pin which automatically locks the furling apparatus when the device is furled and unfurled. Thus, in order to furl an unfurled device, the locking pin must be disengaged; likewise, in order to unfurl a furled device, the locking pin must be disengaged.

This locking mechanism includes a pair of lock sleeves 74 and springs 76 positioned within two bores 78 formed in traveler cylinder 64. As shown best in FIGS. 4 and 5, the lock sleeves 74 and springs 76 work in combination with a release plunger 80, release plunger sleeve 82, and release button 84 secured to traveler housing 70. The release plunger 80 fits within plunger sleeve which is configured to fit within a bore 86 formed in traveler housing 70. The release button 84 is secured to the release plunger 80 and is designed to be depressed by the user.

When either lock sleeve 74 is in alignment with release plunger 80, spring 76 causes the respective lock sleeve 74 to engage the release plunger sleeve 82 and thereby lock the traveler cylinder 64 relative to the traveler housing 70. Depressing release button 84 disengages the lock sleeve 74 from release plunger sleeve 82, thereby permitting the traveler cylinder 64 to be rotated relative to the traveler housing 70.

In assembling furling apparatus 40, a hollow extension housing 88 is rotatably attached to traveler housing 70. At the distal end of the extension housing 88 is a circular groove 90 cut in the inside wall thereof. The circular groove 90 is designed to snap around a bevelled rim 92 formed at the proximal end of traveler housing 70. Thus assembled the internal working parts of the furling apparatus are tamper proof.

The extension housing 88 also includes two longitudinal grooves 94 formed on the inside wall thereof. A pair of groove tracking pins 96 located on the outer periphery of collet 50 are configured to fit within the longitudinal grooves 94 such that twisting the extension housing 88 will also twist collet 50. The combination of tracking pins 96 and longitudinal grooves 94 permits collet 50 (and locking hub 52 attached thereto) to longitudinally slide within extension housing 88.

In practice, the furling apparatus is attached to the extrapulmonary blood oxygenator by engaging the proximal ends of the outer and inner lumen as described above. When the oxygenator is unfurled, as shown in FIGS. 1 and 4, the locking hub 52 is accessible to engage the inner lumen 26. One lock sleeve 74 also engages release plunger sleeve 82, such that in order to twist the extension housing 88 (which engages collet 50 which is secured to traveler cylinder 64 by leadscrew 60), release button 84 must be depressed. After depressing release button 84, twisting extension housing 88 causes leadscrew 60 to threadably pass through leadscrew nut 68. This movement causes the gas permeable tubes to be twisted and elongated and at the same time causes locking hub 52 to retract within extension housing 88.

At the point where the hollow fiber bundle is fully twisted into an insertion diameter, as shown in FIGS. 2 and 5, one lock sleeve 74 again engages release plunger sleeve 82, such that further twisting of the extension housing 88 is prohibited. The locking hub 52 is retracted within extension housing 88 such that it is not possible to disengage the inner lumen. This important feature prevents sudden or undesired unfurling of the hollow fiber bundle.

Another important feature of the present invention is the ability to removably insert stylet 98 within the inner lumen even when the gas permeable tubes are twisted into an insertion diameter. It has been found that the closer the distal end of the stylet gets to the distal chamber, the stiffer the distal end of the in vivo extrapulmonary oxygenation apparatus becomes. Thus, the rigidity of the apparatus may be adjusted, even during insertion, by sliding the stylet in or out of the inner lumen.

C. Apparatus Tip and Guidewire Insertion Method

The extrapulmonary blood oxygenator illustrated in FIGS. 1 and 2 is designed to be inserted through a single incision into the right external iliac vein, right femoral vein, or right jugular vein. Prior to insertion within the venae cavae the overall diameter of the bundle of gas permeable tubes is reduced as best illustrated in FIG. 2. The insertion diameter is formed by twisting and elongating the gas permeable tubes as discussed above.

Before inserting the oxygenator within the patient, guidewire 100 is preferably inserted within the venae cavae. Proper positioning of the guidewire is preferably verified using fluoroscopy or x-rays. One currently preferred guidewire is about 150 cm long. The distal end of the guidewire preferably includes a "J-tip" coiled spring configuration, similar to those known in the art. The "J-tip" configuration helps protect sensitive vascular tissues from trauma caused the sharp point of the guidewire.

Unlike conventional guidewire used in the art, the guidewire for inserting the extrapulmonary blood oxygenator is preferably relatively rigid along most of its length. Guidewire rigidity is important in order to advance the tip of the oxygenator into difficult locations. Of course some flexibility is necessary in order to pass through non-linear vascular passageways. One currently preferred guidewire, having the flexible "J-tip" at its distal end, is relatively flexible for approximately 30 cm at its distal end. For the remaining 120 cm, the guidewire is constructed of solid stainless steel rod. This configuration is in contrast to existing guidewires which are often coiled spring configurations.

The distal tip of the extrapulmonary blood oxygenator is preferably configured to form an airtight distal chamber around the distal ends of the gas permeable tubes and configured so that the guidewire may pass through the tip. In this way, the oxygenator tip is inserted over the guidewire during the insertion process and the guidewire remains substantially exterior of the blood oxygenator. As shown in FIGS. 1, 2, and 6, distal tip 102 defines a guidewire conduit 104. The guidewire conduit 104 has a distal opening 106 and a proximal opening 108 such that the guidewire conduit 104 is not in gaseous communication with the plurality of gas permeable tubes 14. Ideally, the guidewire conduit 104 is substantially parallel to the longitudinal axis of the oxygenator. However, in practice, the guidewire conduit will usually not be parallel to the longitudinal axis of the oxygenator.

The overall configuration of distal tip 102 is to permit the distal tip to follow the guidewire during insertion with minimal trauma to the sensitive vascular tissues. One important feature of the distal tip configuration is the angle between the guidewire and leading surface 110. This angle is preferably greater than 90°. If the angle were less than 90°, then the distal tip could snare and possibly harm vascular structures during insertion of the oxygenator.

The distal tip is preferably constructed of a material which is hard enough to track the guidewire, yet not so soft that it will deflect and bind the guidewire. It is currently preferred that the distal tip be constructed of a material having a hardness in the range from about 83 to about 88 Shore-A, with a hardness of about 85 Shore-A being most preferred. The distal tip is also preferably constructed of a biocompatible material which possesses thrombo-resistant properties. Polyurethane is a currently preferred material for constructing the distal tip.

In one embodiment within the scope of the present invention, shown best in FIGS. 6 and 7, a metal wire 112 is positioned within the inner lumen 26. Wire 112 preferably extends from the distal chamber 30 to a point proximal of the proximal chamber 28. The wire provides structural support for the hollow fiber bundle 12 in addition to the inner lumen 26 and the spacer lumen 32. In this way, the apparatus is readily maintained in the proper position within the venae cavae. A bend 114 in wire 112 keeps the wire in proper position within the inner lumen.

As shown in FIG. 7, stylet 98 is preferably hollow at its distal end such that the wire 112 is capable of being positioned within the stylet. The distal end 116 of the stylet is shaped so that the proximal end 118 of the wire will readily slide within the stylet. In this way, the stylet may be inserted within the inner lumen without being obstructed by the wire.

For safety reasons it is important to hydrate the gas permeable tubes and to remove any air bubbles which might remain between the individual tubes prior to inserting the device within the venae cavae.

Once the oxygenator is in place, inner lumen 26 preferably will be connected to a source of oxygen-enriched gas and outer lumen 24 preferably will be connected to a vacuum or some other exhaust means. As a result, oxygen-enriched gas will travel through the inner lumen 26 into distal chamber 30 and there into the distal ends 16 of the gas permeable tubes 14.

During the time the oxygen-enriched gas is within the gas permeable tubes it will be able to oxygenate the blood traveling through the venae cavae. In addition, carbon dioxide will be able to pass from the blood into the gas permeable tubes and thereby be removed from the blood stream. As discussed above, oxygen and carbon dioxide can readily travel through the walls of gas permeable tubes 14, but blood cannot enter the tubes. Thus, oxygenation can occur without the blood being directly exposed to gas bubbles.

After the gas has passed through the gas permeable tubes, the gas is released within proximal chamber 28 which narrows to form outer lumen 24 in the embodiment illustrated in FIG. 7. The gas flows through the outer lumen and is removed from the device.

It is presently preferred that the device is operated at subatmospheric pressures. Currently, nearly 100% oxygen is introduced into the proximal end of inner lumen 26 at about atmospheric pressure. A vacuum is attached to the outer lumen 24 to provide the necessary pressure difference to cause the oxygen gas to flow through the gas permeable tubes. The oxygen gas experiences a pressure drop as it flows through the inner lumen 26 towards the distal chamber 30. As a result, the pressure of the oxygen gas as it enters the distal end 18 of the gas permeable tubes is subatmospheric.

Operation of the device at such low pressures will enhance carbon dioxide removal, yet also provide adequate blood oxygenation. The driving force behind blood gas transfer in the present invention is the difference between the partial pressures of the oxygen and carbon dioxide in the blood stream and the partial pressures of the oxygen and carbon dioxide in the gas permeable tubes. Lowering the pressure within the gas permeable tubes necessarily promotes transfer of carbon dioxide from blood into the gas permeable tubes. On the other hand, lowering the pressure within the gas permeable tubes reduces the partial pressure of oxygen in the gas permeable tubes. But because nearly pure oxygen is used, the partial pressure of oxygen is still sufficiently high to achieve adequate blood oxygenation.

Traditionally, blood oxygenation has been the primary goal in patients suffering from acute respiratory failure. However, it has been found that removal of carbon dioxide from blood is also important. Thus, operation of the device at subatmospheric pressures enhances the overall effectiveness of the device.

Moreover, since the operating pressure is preferably less than the blood pressure, any leak in the device cannot introduce air bubbles within the blood stream. Any such leak would introduce blood within the gas permeable tubes, rather than allow gas to enter the blood stream. Therefore, operation of the device at subatmospheric pressures provides significant safety benefits.

Although the above discussion has described oxygen being introduced through the inner lumen 26, it will be appreciated that the device can be also operated with oxygen being introduced through the outer lumen 24 and into the proximal chamber 28, with oxygen then flowing through the gas permeable tubes and into the distal chamber 30, and finally being removed through the inner lumen 26. Oxygen introduced through the outer lumen 24 is preferably at a subatmospheric pressure to compensate for the pressure drop across the inner lumen 26.

In summary, the method and apparatus disclosed herein is a significant improvement to the extrapulmonary blood oxygenator described in U.S. Pat. No. 4,850,958. In the present invention a stylet is not required to engage and twist the distal end of the device in order to form an insertion diameter or an oxygenation diameter. In this way the flexibility of the distal end of the oxygenator may be adjusted even during insertion.

Additionally, it will be appreciated that the present invention to provides an apparatus for furling an intravenous blood gas exchange device which indicates when the device is fully furled and fully unfurled, thereby reducing the risk of potential damage to the gas permeable tubes caused by over-twisting. The furling apparatus within the scope of the present invention also prevents sudden and undesired unfurling of the bundle of gas permeable tubes.

Likewise, it will be appreciated that the present invention provides apparatus for in vivo blood oxygenation capable of being inserted with an over-the-guidewire insertion method. The distal tip of the oxygenator is capable of being adapted for use with other intravascular devices which are inserted within a patient.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. An apparatus for twisting one lumen of a coaxial lumen device relative to the other lumen comprising:
    elastomeric means for selectively engaging without collapsing a proximal end of one of an inner lumen and an outer lumen of said coaxial lumen device;
    means for selectively engaging a proximal end of the other of said inner and outer lumens of said coaxial lumen device; and
    means for twisting said inner lumen relative to said outer lumen.

2. An apparatus for twisting one lumen of a coaxial lumen device relative to the other lumen as defined in claim 1, wherein the means for removably engaging the inner lumen comprises a compressible gasket adapted to be positioned around the inner lumen such that the inner lumen is engaged upon compression of said gasket.

3. An apparatus for twisting one lumen of a coaxial lumen device relative to the other lumen as defined in claim 2, further comprising means for compressing the compressible gasket.

4. An apparatus for twisting one lumen of a coaxial lumen device relative to the other lumen as defined in claim 3, wherein the means for removably engaging the outer lumen comprises a luer connector.

5. An apparatus for twisting one lumen of a coaxial lumen device relative to the other lumen as defined in claim 4, further comprising a stationary housing and wherein the luer connector is secured to the stationary housing.

6. An apparatus for twisting one lumen of a coaxial lumen device relative to the other lumen as defined in claim 5, wherein the stationary housing is threadably attached to the means for compressing the compressible gasket such that threading the compressing means relative to the stationary housing simultaneously twists the inner lumen relative to the outer lumen.

7. An apparatus for twisting one lumen of a coaxial lumen device relative to the other lumen as defined in claim 6, wherein the stationary housing comprises means for locking the compressing means relative to the stationary housing.

8. An apparatus for twisting one lumen of a coaxial lumen device relative to the other as defined in claim 1, wherein the inner lumen has a noncircular inner surface cross-sectional configuration and wherein the means for removably engaging the proximal end of the inner lumen comprises a hollow mandrel having a matching noncircular outer surface cross-sectional configuration such that the mandrel is capable of removably engaging the proximal end of the inner lumen.

9. An apparatus for furling an intravenous oxygenation device having a plurality of gas permeable tubes in gaseous communication with an inner and an outer lumen of a coaxial lumen tube, said furling apparatus providing either an insertion diameter when inserting said oxygenation device into the venae cavae of a patient or an oxygenation diameter after said oxygenation device is positioned within the venae cavae, said furling apparatus comprising:
    a stationary housing having means for selectively engaging and disengaging a proximal end of said outer lumen; and
    a twisting member having means for selectively engaging and disengaging a proximal end of said inner lumen, said twisting member being rotatably connected to said stationary member, such that when said twisting member is rotated in a first direction, said inner lumen will be engaged and twisted relative to said outer lumen and said gas permeable tubes will be twisted into said insertion diameter, and when said twisting member is rotated in a counter direction said inner lumen will be disengaged and untwisted relative to said outer lumen and said gas permeable tubes will be unfurled into said oxygenation diameter.

10. An apparatus for furling an intravenous oxygenation device as defined in claim 9, wherein said means for selectively engaging a proximal end of said outer lumen comprises a luer connector.

11. An apparatus for furling an intravenous oxygenation device as defined in claim 9, wherein said means for selectively engaging a proximal end of said inner lumen comprises a compressible gasket adapted to be positioned around the inner lumen such that the inner lumen is engaged upon compression of said gasket.

12. An apparatus for furling an intravenous oxygenation device as defined in claim 11, wherein the twisting member further comprises means for compressing the compressible gasket.

13. An apparatus for furling an intravenous oxygenation device as defined in claim 12, wherein the twisting member is threadably connected to said stationary member.

14. An apparatus for furling an intravenous oxygenation device as defined in claim 13, wherein the means for compressing the compressible gasket comprises a means that is retracted into the twisting member upon rotating the twisting member relative to the stationary member.

15. An apparatus for furling an intravenous oxygenation device as defined in claim 9, wherein the stationary housing comprises means for locking the twisting member relative to the stationary housing.

16. An apparatus for furling an intravenous oxygenation device as defined in claim 15, wherein the locking means comprises a means that is engaged at the point the gas permeable tubes are fully furled into an insertion diameter and at the point the gas permeable tubes are fully unfurled into an oxygenation diameter.

17. An apparatus for furling an intravenous oxygenation device as defined in claim 9, wherein the inner lumen has a noncircular inner surface cross-sectional configuration and wherein the means for removably engaging the proximal end of the inner lumen comprises a hollow mandrel having a matching noncircular outer surface cross-sectional configuration such that the mandrel is capable of removably engaging the proximal end of the inner lumen.

18. An apparatus for effecting in vivo extrapulmonary blood gas exchange whereby blood flowing through the venae cavae of a patient receives oxygen and releases carbon dioxide, the apparatus comprising:
    a plurality of elongated gas permeable tubes, each tube having a proximal end and a distal end, said gas permeable tubes forming a gas permeable tube bundle;
    means for enclosing the proximal ends of the gas permeable tubes so as to form an airtight proximal chamber;
    means for enclosing the distal ends of the gas permeable tubes so as to form an airtight distal chamber;
    a dual lumen tube having an outer lumen and an inner lumen which runs coaxially through said outer lumen, said outer lumen terminating and opening within the proximal chamber such that said outer lumen is in gaseous communication with the proximal ends of the gas permeable tubes, said inner lumen terminating and opening within the distal chamber such that said inner lumen is in gaseous communication with the distal ends of the gas permeable tubes;
    means for binding the gas permeable tubes together at each end, wherein the inner lumen is nonrotatably anchored to the binding means of said distal ends and the outer lumen is nonrotatably anchored to the binding means of said proximal ends;
    a spacer lumen nonrotatably anchored to the binding means of said proximal and distal ends, said spacer lumen being coaxial with said inner lumen such that said inner lumen runs coaxially through said spacer lumen; and means for selectively adjusting the overall diameter of the gas permeable tube bundle so as to be able to adjust said diameter to provide either an insertion diameter when inserting said apparatus into the venae cavae, or an oxygenation diameter after said apparatus is in place within the venae cavae, said means comprising:

means for removably engaging a proximal end of said inner lumen;

means for removably engaging a proximal end of said outer lumen;

means for twisting said inner lumen relative to said outer lumen such that the gas permeable tubes are placed in either a twisted state, thereby forming an insertion diameter, or an untwisted state, thereby forming an oxygenation diameter said means for twisting the inner lumen relative to the outer lumen comprising a stationary housing removably attached to the outer lumen and a twisting member rotatably engaged with said stationary housing, such that twisting of said twisting member relative to said stationary housing twists the gas permeable tubes while holding the binding means at one of the proximal and distal ends essentially stationary relative to the other.

19. An apparatus as defined in claim 18, wherein said means for removably engaging the proximal end of the inner lumen comprises a compressible gasket adapted to be positioned around the inner lumen such that the inner lumen is engaged upon compression of said gasket.

20. An apparatus as defined in claim 18, wherein the twisting member further comprises means for compressing the compressible gasket.

21. An apparatus as defined in claim 20, wherein the means for compressing the compressible gasket comprises a means that is retracted into the twisting member upon rotating the twisting member relative to the stationary member.

22. An apparatus as defined in claim 18, wherein the stationary housing comprises means for locking the twisting member relative to the stationary housing.

23. An apparatus as defined in claim 22, wherein the locking means comprises a mans that is engaged at the point the gas permeable tubes are fully furled into an insertion diameter and at the point the gas permeable tubes are fully unfurled into an oxygenation diameter.

24. An apparatus as defined in claim 18, wherein the spacer lumen is flexible enough to be twisted about a longitudinal axis thereof as the binding means at one of the proximal and distal ends is twisted relative to the other such that when so twisted and held in the twisted state, the spacer lumen provides a spring-like action to aid in untwisting the gas permeable tubes to form said oxygenation diameter.

25. An apparatus as defined in claim 18, wherein the inner lumen has a noncircular inner surface cross-sectional configuration and wherein the means for removably engaging the proximal end of the inner lumen comprises a hollow mandrel having a noncircular outer surface cross-sectional configuration such that the mandrel is capable of removably engaging the proximal end of the inner lumen.

26. An apparatus as defined in claim 18, further comprising a stylet capable of removable insertion through the inner lumen even when the gas permeable tubes are in the twisted state.

27. An apparatus as defined in claim 26, further comprising a wire extending from the distal chamber through the inner lumen to a point proximal of the proximal chamber.

28. An apparatus as defined in claim 27, wherein a portion of the stylet is hollow, said stylet having an inside diameter greater than the diameter of the wire such that the wire fits within the stylet.

29. A medical apparatus for over-the-guidewire insertion into a patient comprising:

a tip located at a distal end of a medical apparatus adapted for intravascular insertion into a patient, wherein said tip occludes the distal end of the medical apparatus, said medical apparatus defining a longitudinal axis; and a guidewire conduit defined by said tip extending from a distal conduit opening on said tip to a proximal conduit opening on said tip, said conduit having a size sufficiently large to permit passage of a guidewire through said conduit, said conduit being displaced from the longitudinal axis of said medical apparatus such that the guidewire capable of passage through said conduit remains substantially offset from the longitudinal axis of said medical apparatus during insertion.

30. A medical apparatus as defined in claim 29, wherein said medical apparatus comprises an apparatus for intravenous oxygenation of blood.

31. A medical apparatus as defined in claim 30, wherein the apparatus for intravenous oxygenation of blood comprises a plurality of gas permeable tubes in gaseous communication with an inner and an outer lumen of a coaxial lumen tube.

32. A medical apparatus as defined in claim 29, wherein said medical apparatus comprises an apparatus for introducing fluids into the patient.

33. A medical apparatus as defined in claim 29, wherein said medical apparatus comprises an apparatus for removing fluids from the patient.

34. An apparatus for effecting in vivo extrapulmonary blood gas exchange whereby blood flowing through the venae cavae of a patient receives oxygen and releases carbon dioxide, the apparatus comprising:

a plurality of elongated gas permeable tubes, each tube having a proximal end and a distal end, said gas permeable tubes forming a gas permeable tube bundle, said gas permeable tube bundle defining a longitudinal axis of the apparatus;

means for enclosing the proximal ends of the gas permeable tubes so as to form an airtight proximal chamber;

means for enclosing the distal ends of the gas permeable tubes so as to form an airtight distal chamber;

a conduit defined by said means for enclosing the distal ends extending from a distal conduit opening on said enclosing means to a proximal conduit opening on said enclosing means, said conduit having a size sufficiently large to permit passage over a guidewire inserted within the patient, said conduit being displaced from the longitudinal axis of said apparatus such that the guidewire capable of passage through said conduit remains substantially offset from the longitudinal axis of said apparatus during insertion;

a dual lumen tube having an outer lumen and an inner lumen which runs coaxially through said outer lumen, said outer lumen terminating and opening within the proximal chamber such that said outer lumen is in gaseous communication with the proximal ends of the gas permeable tubes, said inner lumen terminating and opening within the distal chamber such that said inner lumen is in gaseous communication with the distal ends of the gas permeable tubes;

means for binding the gas permeable tubes together at each end, wherein the inner lumen is nonrotatably anchored to the binding means of said distal ends and the outer lumen is nonrotatably anchored to the binding means of said proximal ends; and means for selectively adjusting the overall diameter of the gas permeable tube bundle so as to be able to adjust said diameter to provide either an insertion diameter when inserting said apparatus into the venae cavae, or an oxygenation diameter after said apparatus is in place within the venae cavae.

35. An apparatus as defined in claim 34, further comprising a stylet capable of removable insertion through the inner lumen even when the diameter of the gas permeable tube bundle is an insertion diameter.

36. An apparatus as defined in claim 34, further comprising a wire extending from the distal chamber through the inner lumen to point proximal of the proximal chamber.

37. An apparatus as defined in claim 34, further comprising:
a wire extending from the distal chamber through the inner lumen to point proximal of the proximal chamber; and
a hollow stylet capable of removable insertion through the inner lumen even when the diameter of the gas permeable tube bundle is an insertion diameter, said stylet having an inside diameter greater than the diameter of the wire such that the wire fits within the stylet.

38. A method for effecting in vivo extrapulmonary blood gas exchange using an apparatus for in vivo extrapulmonary blood gas exchange comprising a plurality of gas permeable tubes comprised of inlet ends and outlet ends, said inlet ends being in gaseous communication with one of an outer and an inner lumen and the outlet ends being in gaseous communication with the other said lumen, said inner lumen running coaxially through said outer lumen, said method comprising the steps of:
reducing the overall diameter of said gas permeable tubes to form an overall insertion diameter with respect to said plurality of tubes, said reducing step comprising the steps of:
engaging and holding stationary a proximal end of the outer lumen; and
engaging and twisting a proximal end of the inner lumen relative to said outer lumen so that the gas permeable tubes are twisted together to form said insertion diameter;
inserting the gas permeable tubes within the venae cavae of a patient through a single venous incision sized to accommodate said insertion diameter;
enlarging the overall diameter of said plurality of gas permeable tubes once they are within said venae cavae to form an oxygenation diameter; and
passing oxygen enriched gas through the gas permeable tubes at subatmospheric pressure such that blood flowing through the venae cavae is oxygenated as carbon dioxide is removed from the blood into the gas permeable tubes.

39. A method as defined in claim 38, further comprising the step of maintaining the gas permeable tubes in a spaced relation one from another when said oxygenation diameter is formed so that blood surface contact with the gas permeable tubes is maximized and such that laminar blood flow in and around the gas permeable tubes is inhibited.

40. A method as defined in claim 38, wherein the step of enlarging the diameter of the gas permeable tubes comprises the steps of:
untwisting the inner lumen relative to said outer lumen so that the gas permeable tubes are untwisted and spaced apart from each other to form an oxygenation diameter;
disengaging the proximal end of the inner lumen; and
disengaging the proximal end of the outer lumen.

41. A method as defined in claim 38, wherein the step of inserting the gas permeable tubes within the venae cavae comprises the steps of:
positioning an introducer within said incision;
hydrating the gas permeable tubes within an aqueous solution to completely remove any bubbles adhering to the surface of the gas permeable tubes; and
passing the gas permeable tubes through the introducer and into the venae cavae of a patient.

42. A method as defined in claim 38, wherein the step of inserting the gas permeable tubes within the venae cavae comprises the steps of:
introducing a guidewire into said incision; and
passing the apparatus for in vivo extrapulmonary blood gas exchange over said guidewire and into the venae cavae of a patient.

43. An apparatus for effecting in vivo extrapulmonary blood gas exchange whereby blood flowing through the venae cavae of a patient receives oxygen and releases carbon dioxide, the apparatus comprising:
a plurality of elongated gas permeable tubes, each tube having a proximal end and a distal end, said gas permeable tubes forming a gas permeable tube bundle, said gas permeable tube bundle defining a longitudinal axis of the apparatus;
means for enclosing the proximal ends of the gas permeable tubes so as to form an airtight proximal chamber;
means for enclosing the distal ends of the gas permeable tubes so as to form an airtight distal chamber;
a conduit defined by said means for enclosing the distal ends extending from a distal conduit opening on said enclosing means to a proximal conduit opening on said enclosing means, said conduit having a size sufficiently large to permit passage over a guidewire inserted within the patient, said conduit being displaced from the longitudinal axis of said apparatus such that the guidewire capable of passage through said conduit remains substantially offset from the longitudinal axis of said apparatus during insertion;
a dual lumen tube having an outer lumen and an inner lumen which runs coaxially through said outer lumen, said outer lumen terminating and opening within the proximal chamber such that said outer lumen is in gaseous communication with the proximal ends of the gas permeable tubes, said inner lumen terminating and opening within the distal chamber such that said inner lumen is in gaseous communication with the distal ends of the gas permeable tubes;

means for binding the gas permeable tubes together at each end, wherein the inner lumen is nonrotatably anchored to the binding means of said distal ends and the outer lumen is nonrotatably anchored to the binding means of said proximal ends; and means for selectively adjusting the overall diameter of the gas permeable tube bundle so as to be able to adjust said diameter to provide either an insertion diameter when inserting said apparatus into the venae cavae, or an oxygenation diameter after said apparatus is in place within the venae cavae, said means comprising:

means for removably engaging a proximal end of said inner lumen;

means for removably engaging a proximal end of said outer lumen;

means for twisting said inner lumen relative to said outer lumen such that the gas permeable tubes are placed in either a twisted state, thereby forming an insertion diameter, or an untwisted state, thereby forming an oxygenation diameter.

* * * * *

UNITED STATES PATENT AND TRADEMARK OFFICE
CERTIFICATE OF CORRECTION

PATENT NO. : 5,098,376

DATED : March 24, 1992

INVENTOR(S) : GAYLORD L. BERRY et al.

It is certified that error appears in the above-identified patent and that said Letters Patent is hereby corrected as shown below:

```
Column 3, line 18, "guide wire" should be --guidewire--
Column 7, line 47, "are" should be --is--
Column 9, line 30, after "locking hub" insert --52--
Column 10, lines 60-61, after "plunger sleeve" insert --82--
Column 10, line 65, delete "either"
Column 12, line 6, after "caused" insert --by--
Column 13, line 17, "and there" should be --and from there--
Column 14, line 27, delete "to"
Column 17, line 16, after "diameter" insert --,--
Column 17, line 44, "mans" should be --means--
```

Signed and Sealed this

Twenty-fourth Day of August, 1993

Attest:

Attesting Officer

BRUCE LEHMAN

Commissioner of Patents and Trademarks